(12) United States Patent
Nissenkorn

(10) Patent No.: US 7,036,511 B2
(45) Date of Patent: May 2, 2006

(54) VAGINAL PESSARY

(76) Inventor: Abraham Nissenkorn, P.O. Box 5269, Holon, 58125 (IL)

( * ) Notice: Subject to any disclaimer, the term of this patent is extended or adjusted under 35 U.S.C. 154(b) by 0 days.

(21) Appl. No.: 10/495,483

(22) PCT Filed: Nov. 13, 2002

(86) PCT No.: PCT/IL02/00908

§ 371 (c)(1),
(2), (4) Date: May 13, 2004

(87) PCT Pub. No.: WO03/047476

PCT Pub. Date: Jun. 12, 2003

(65) Prior Publication Data

US 2005/0016545 A1   Jan. 27, 2005

(30) Foreign Application Priority Data

Nov. 15, 2001 (IL) .................................. 146534

(51) Int. Cl.
*A61F 6/06* (2006.01)
(52) U.S. Cl. ...................................... 128/834; 128/836
(58) Field of Classification Search ............. 128/830, 128/834, 836, 837
See application file for complete search history.

(56) References Cited

U.S. PATENT DOCUMENTS

| 4,261,352 A | 4/1981 | Sedlacek |
| 4,823,814 A | 4/1989 | Drogendijk et al. |
| 5,007,894 A | 4/1991 | Enhorning |
| 5,894,842 A * | 4/1999 | Rabin et al. ................ 128/830 |

FOREIGN PATENT DOCUMENTS

| DE | 600 304 | 1/1933 |
| DE | 198 16349 A1 | 10/1999 |
| GB | 1115727 | 5/1968 |
| NL | 8 500 470 | 9/1986 |

* cited by examiner

*Primary Examiner*—Henry Bennett
*Assistant Examiner*—Camtu Nguyen
(74) *Attorney, Agent, or Firm*—Nath & Associates; Gregory B. Kang; Teresa M. Arroyo

(57) ABSTRACT

An adjustable vaginal pessary (2) comprising a body (4) with an outer periphery, and an inner periphery defining an aperture (10). The pessary further comprises at least one adjustable portion (12,13) located on the body between said inner and out peripheries. The adjustable portion is bounded by two ends (12a, 12b, 13a, 13b) of the body interfacing therewith. T portion is adapted to vary the distance between the two ends in the direction along the body's perimeter, thereby adjusting the length of the peripheries.

12 Claims, 2 Drawing Sheets

VAGINAL PESSARY

FIELD OF THE INVENTION

This invention relates to vaginal pessaries used for treating pelvic genital organ prolapse and female urinary distress, including stress incontinence.

BACKGROUND OF THE INVENTION

Vaginal pessaries are suppositories that provide support to the vaginal walls and are intended to treat pelvic genital organ prolapse and urinary distress in women, including stress incontinence. Such pessaries vary in size and an appropriate size is typically chosen and fitted by a doctor according to an individual patient's anatomy.

U.S. Pat. No. 4,823,814 discloses a flexible ring-shaped pessary made of a specific material enabling the ring's shape can be deformed by hand and the ring's circumference can be increased or decreased to some extent to suit various types and stages of prolapse.

U.S. Pat. No. 5,007,894 discloses a device for treating female incontinence comprising an annular body, which is fully inflated when it is positioned within the vagina to counteract prolapse and prevent incontinence but which may also be deflated to facilitate insertion or removal of the device.

SUMMARY OF THE INVENTION

The present invention suggests a vaginal pessary whose perimeter can be adjusted to suit a variety of women and can be easily inserted by the woman herself, thereby eliminating the necessity of a medical examination to determine an appropriate pessary size or the aid of a trained health professional to perform its insertion. The adjustable vaginal pessary according to the present invention comprises a body with an outer periphery and an inner periphery defining an aperture, and an adjustable portion located on said body between said inner and outer peripheries and being bounded by two ends of said body interfacing therewith, said portion being adapted to vary the distance between said two ends in the direction along the body's perimeter, thereby adjusting the length of said peripheries.

The adjustable vaginal pessary according to the present invention is particularly useful in the treatment of pelvic genital organ prolapse and female urinary distress, including stress incontinence, and thereby also the ill-effects that arise therefrom. Since its size can be adjusted, the adjustable pessary of the present invention can replace a large majority of the range of currently produced pessary sizes, and because it does not utilize complicated adjusting mechanisms, the pessary of the present invention requires little time and effort to insert and fit into the vagina as well as remove therefrom. The latter advantage of the present invention allows a user to insert, remove, and fit the pessary herself, thereby eliminating the need for the repeated assistance of a doctor or other such skilled health professional and, with it, the inconvenience and embarrassment which often accompany the receipt of such assistance. In addition, in many cases, there is the added benefit of a more sensitive and comfortable insertion and removal since this can be performed by the user herself.

The pessary of the present invention may be adjusted to the user's size before insertion into the vagina, or after the pessary is positioned in the desired functional location within the vagina. The size of the pessary can also be reduced to facilitate its insertion. Also, the ability of the pessary of the present invention to vary its size affords convenience to the user as it can be easily adjusted to provide varying degrees of support to suit the user's expected activities. In addition, the pessary of the present invention is able to accommodate a change in a user's anatomical or medical situation requiring the need for a different size.

The pessary of the present invention is suitable for women of all ages, and is especially suitable for women who are non-candidates for surgery. Also, due to its many advantages, the pessary of the present invention constitutes a more attractive alternative to surgery than currently available non-adjusting pessaries.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
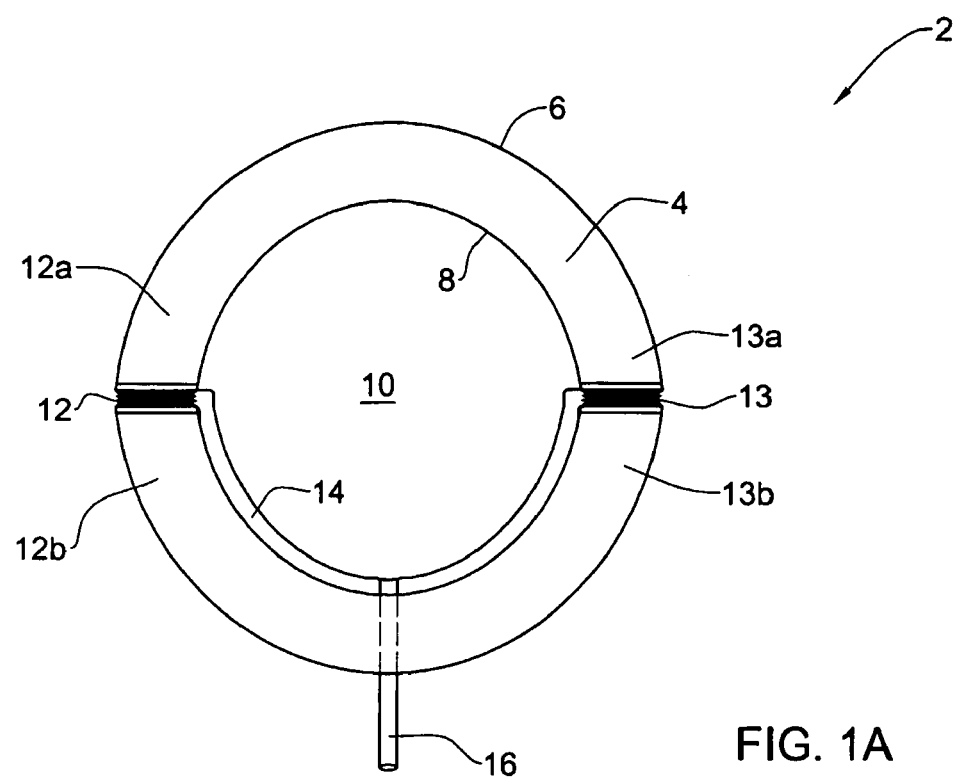
FIG. 1A shows a pessary according to the present invention in a retracted position.

FIG. 1A schematically shows an adjustable vaginal pessary 2 according to the present invention, which is to be inserted into a vagina to provide support therein. The pessary 2 is annular and comprises a body 4 with an outer periphery 6 and an inner periphery 8 defining an aperture 10. While rounded shapes are preferable, the pessary 2 may have any closed geometry so long as it contains the aperture 10.

The body 4 further comprises two adjustable portions 12 and 13 both located between the inner and outer peripheries 6 and 8. The adjustable portion 12 is bounded by two ends 12a and 12b of the body 4 that interface therewith. Likewise, on the diametrically opposed side of the body 4, the adjustable portion 13 is bounded by two interfacing ends 13a and 13b. Each adjustable portion 12, 13 is inflatable and is adapted to vary the distance between its two ends 12a, 12b, and 13a, 13b in the direction of the circumference of the body 4. Being of a foldable accordion-like shape, the adjustable portions 12 and 13 are able to expand in the direction along the body's perimeter when inflated. In this way, the length of the peripheries 6 and 8 may be adjusted. It should be noted that the pessary 2 may include a single adjustable portion or a plurality thereof and the adjustable portions may be located anywhere on the perimeter of the body 4.

The pessary 2 also includes a conduit 14 in communication with the adjustable portions 12 and 13 for conducting a fluid, which may be a liquid or a gas, thereto. The conduit 14 is adapted to further communicate with an inflation tube 16, which supplies the conduit 14 with the fluid. The inflation tube 16 includes a valve to allow a fluid to enter but prevents its spontaneous escape. The valve may also include a means available to the user permitting instant or gradual deflation of the portions 12 and 13. The tube 16 may be integral and therefore remain attached at all times to the conduit 14, or it may have means or connecting and disconnecting from the conduit 14 when required for inflation and deflation.

Figure 1B:
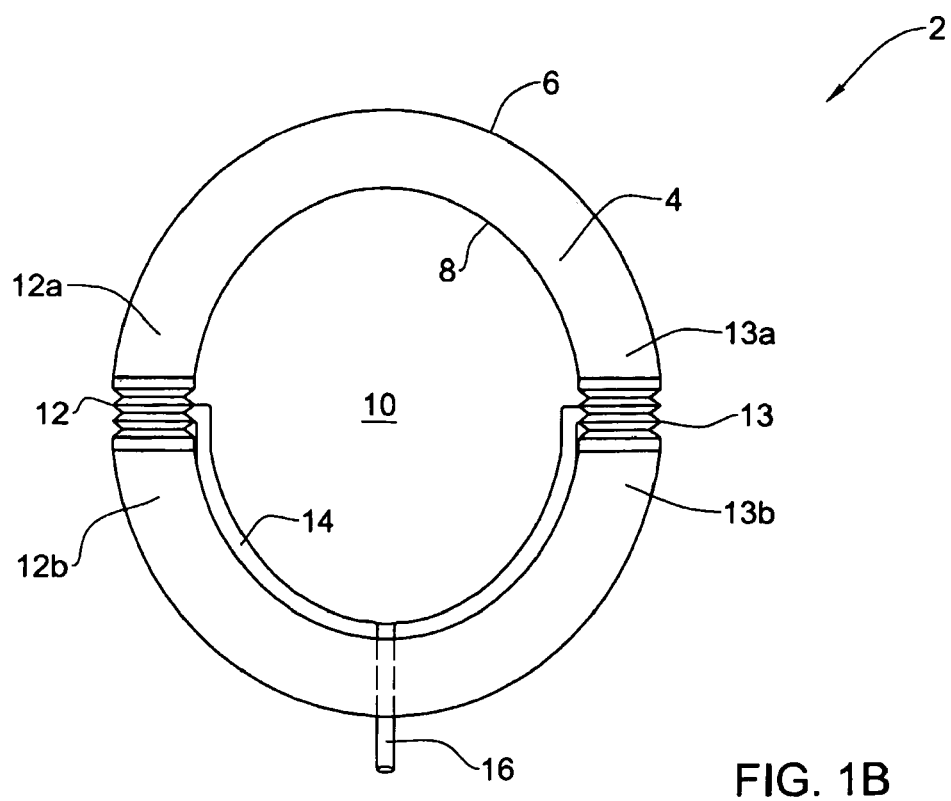
FIG. 1B shows a pessary according to the present invention in an extended position.

FIG. 1A shows the pessary 2 in its retracted position where it has a minimal circumference. In operation, before or after the pessary 2 is inserted into the vagina, fluid is supplied to the adjustable portions 12 and 13 via the inflation tube 16 and the conduit 14 causing these potions 12 and 13, and consequently the circumference of the body 4, to lengthen. FIG. 1B shows the pessary 2 in an extended position with the portions 12 and 13 filled to a certain extent. Fluid continues to be conducted to the portions 12 and 13 until the pessary 2 enlarges to a desired size. The pessary 2 is similarly reduced in size by deflation, in which fluid is removed from the adjustable portions 12 and 13 via the conduit 14.

The adjustable potions 12 and 13 may have any design or shape allowing for the adjustment of the pessary's perimeter. The portions 12 and 13 may be adapted to be fill with fluid throughout the internal space they define, or rather may be adapted to fill only at their walls. The variation of length of the portions 12 and 13 may be achieved by using pneumatic or hydraulic methods as described above, or by any other method such as mechanical means.

Figure 2A:
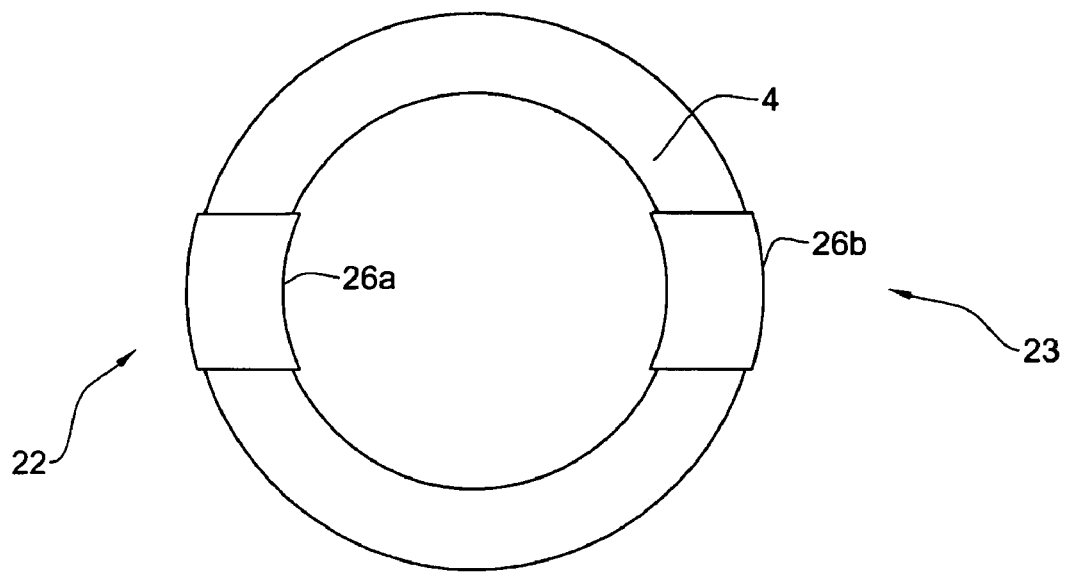
FIG. 2A shows an alternative embodiment for a pessary according to the present invention in a retracted position.
Figure 2B:
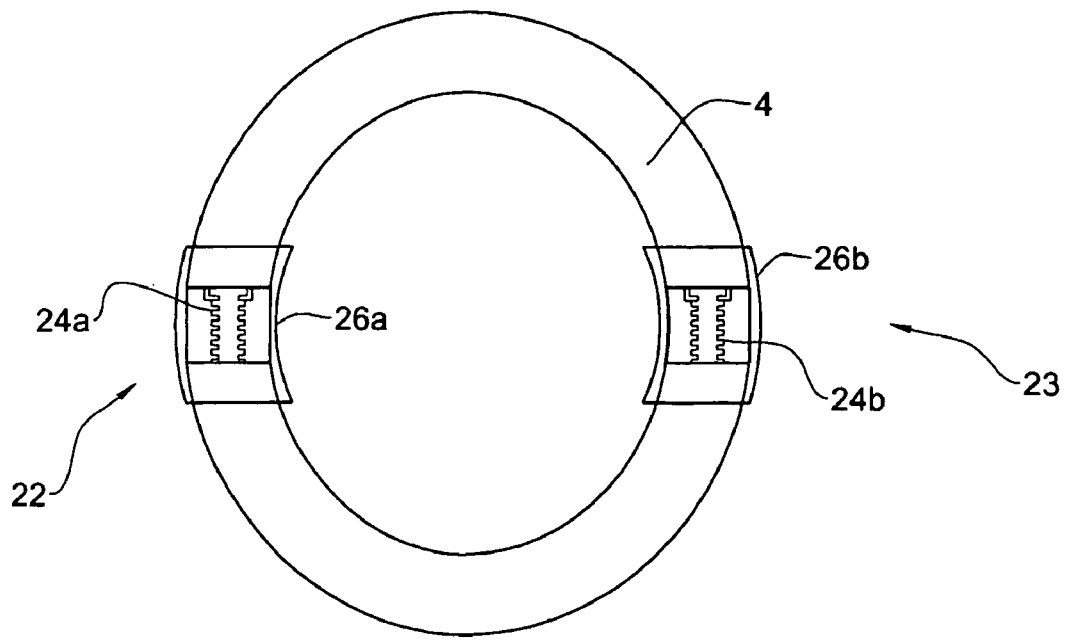
FIG. 2B shows an alternative embodiment for a pessary according to the present invention in an extended position.

FIGS. 2A and 2B show a pessary 2 in a retracted and extended position respectively having adjustable portions 22 and 23 that function mechanically to reduce or augment the pessary's perimeter. The portions 22 and 23 are based on a ratchet mechanism 24a, 24b having teeth enabling gradual adjustment of the pessary's size. The pessary 2 may further comprise a reinforcing sleeves 26a and 26b which add structural support to the indented adjustable portions 22 and 23, but also serve to provide a smoother surface and to protect the user from contacting the surface of the ratchet mechanism 24a, 24b.

Other possible mechanical alternatives for the adjustable potions may include engaging, telescoping parts that slide into one another allowing for length adjustment. Such telescoping mechanisms may include parts that slide within each other or slide in and out of the body 4 of the pessary 2 thereby allowing its size adjustment.

The pessary 2 according to the present invention and its parts may be made of any material that is not harmful to human use. These preferably include materials that do not easily degrade or cause irritation, including medically approved grades of silicone or plastic such as polyethylene and polyvinyl chloride.

It should be understood that the above-described embodiments are only examples of an adjustable vaginal pessary and that the scope of the present invention fully encompasses other embodiments, which may become obvious to those skilled in the art. For example, the pessary may be used to provide support in the treatment of other medical conditions where size variance and adjustment may be useful.

The invention claimed is:

1. An adjustable vaginal pessary adapted to provide support to vaginal walls of a patient, comprising:
a body with an outer periphery defining the perimeter of the body, an inner periphery defining an aperture, at least a pair of ends and an adjustable portion spacing, and interfacing with, said ends, said portion being adapted for adjusting its length in the direction along the perimeter of the body to increase the distance between said ends when said length is increased and to reduce said distance when said length is reduced, thereby adjusting the length of said inner and outer peripheries to provide varying degrees of said support.

2. An adjustable vaginal pessary according to claim 1, having at least two pairs of said ends and said adjustable portion between each pair of said ends.

3. An adjustable vaginal pessary according to claim 1, adapted for use in treating pelvic organ prolapse.

4. An adjustable vaginal pessary according to claim 1, adapted for use in treating stress incontinence.

5. An adjustable vaginal pessary according to claim 1, wherein the adjustable portion comprises pneumatic means for adjusting its length.

6. An adjustable vaginal pessary according to claim 1, wherein the adjustable portion comprises hydraulic means for adjusting its length.

7. An adjustable vaginal pessary according to claim 1, wherein the adjustable portion has a foldable, accordion-like shape to expand when the distance between said ends is to be increased and to fold when said distance is to be reduced.

8. An adjustable vaginal pessary according to claim 1, wherein the adjustable portion comprises mechanical means for adjusting its length.

9. An adjustable vaginal pessary according to claim 8, wherein the mechanical means is a ratchet mechanism.

10. An adjustable vaginal pessary according to claim 8, wherein the mechanical means is a telescoping mechanism.

11. An adjustable vaginal pessary adapted to provide support to vaginal walls of a patient, comprising:
a body with an outer periphery defining the perimeter of the body, an inner periphery defining an aperture, at least a pair of ends and an adjustable portion spacing, and interfacing with, said ends, said portion being connectable to a source of a fluid and being adapted for inflation to increase the length of the portion in the direction along the perimeter of the body and, consequently, to increase the distance between said ends, and for deflation to reduce said length and, consequently, to reduce the distance between said ends, thereby adjusting the length of said inner and outer peripheries to provide varying degrees of said support.

12. An adjustable vaginal pessary adapted to provide support to vaginal walls of a patient, comprising:
a body with an outer periphery defining the perimeter of the body, an inner periphery defining an aperture, at least a pair of ends and an adjustable portion spacing, and interfacing with, said ends, said portion comprising a ratchet mechanism to increase and reduce the length of the portion in the direction along the perimeter of the body and, respectively, to increase and reduce the distance between said ends, thereby adjusting the length of said inner and outer peripheries to provide varying degrees of said support.

\* \* \* \* \*